United States Patent [19]

Deziel et al.

[11] Patent Number: 4,841,043
[45] Date of Patent: Jun. 20, 1989

[54] STEREOSELECTIVE SYNTHESIS OF 1-β-ALKYL CARBAPENEM ANTIBIOTIC INTERMEDIATES

[75] Inventors: Robert Deziel, St. Lambert; Masaki Endo, Candiac, both of Canada

[73] Assignee: Bristol-Myers Company, New York, N.Y.

[21] Appl. No.: 81,054

[22] Filed: Aug. 3, 1987

Related U.S. Application Data

[62] Division of Ser. No. 812,570, Dec. 23, 1985, abandoned.

[51] Int. Cl.$^4$ .............. C07D 205/08; C07B 37/04; C07F 7/22; C07F 7/18
[52] U.S. Cl. .............................. 540/200; 540/357; 540/360; 540/361; 556/87; 556/88; 560/170
[58] Field of Search ............................... 540/200

[56] References Cited

PUBLICATIONS

Shirai, O., J. Org. Chem., 52, 5491(1987).
Terajima, Chem. Abs., 108, 55764f.
Mukaijama, Tetrahedron, 40 1381(1984).

*Primary Examiner*—Mark L. Berch
*Attorney, Agent, or Firm*—Robert E. Carnahan

[57] ABSTRACT

There is disclosed a process for producing carbapenam diazo intermediates of the formula

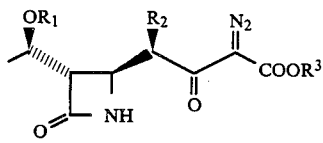

14 wherein
$R^1$ is hydrogen or a hydroxy-protecting group,
$R^2$ is a lower alkyl having from 1–6 carbon atoms, and
$R^3$ represents a conventional carboxyl-protecting group.

The processs comprises alkylating a 4-substituted azetidinone with the tin enolate of an α-bromoketone, in the presence of a silver salt, iodine, or iodine salt as a catalyst, and a strongly polar solvent. The β/α yield of the product diazo intermediate is approximately 3/1.

34 Claims, No Drawings

STEREOSELECTIVE SYNTHESIS OF 1-β-ALKYL CARBAPENEM ANTIBIOTIC INTERMEDIATES

This application is a division of application Ser. No. 812,570 filed Dec. 23, 1985, now abandoned.

BACKGROUND OF THE INVENTION

1. Field of the Invention

The present invention is directed to a novel process for producing intermediates useful in the synthesis of 1-β-alkyl carbapenems.

2. Description of the Prior Art

A wide variety of carbapenems, such as the natural fermentation product thienamycin (Formula I), have been reported in the patent and scientific literature as having exceptional antibacterial activity.

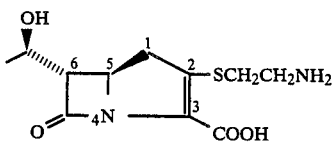

However, researchers attempting to develop thienamycin have encountered two problems, namely: (1) the compound is very difficult to ferment and isolate, and (2) the product is very unstable, such that it reacts with itself and decomposes. To circumvent these problems, carbapenem derivatives have been prepared which possess excellent stability and antibacterial spectra.

One such group of derivatives currently being investigated is the 1-β-methyl carbapenems of the formula:

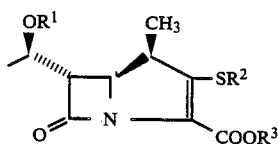

wherein $R^1$ is hydrogen or a conventional hydroxy-protecting group; and $R^2$ and $R^3$ are independently selected from the group consisting of substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hereto atom or atoms in the above-named heterocyclic moieties are selected from the group consisting of 1-4 oxygen, nitrogen and sulfur atoms and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieities of the above-recited substituents have 1-6 carbon atoms.

Recently reported synthetic schemes for producing 1-β-methyl carbapenems of Formula II, such as those of Shih et al., Heterocycles, volume 21, no. 1, pages 29-40 (1984), proceed through diazo intermediates of the formula

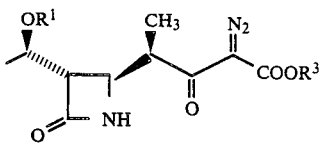

from which the 1-β-methyl carbapenems can be formed easily and in high yield. Unfortunately, however, these schemes require numerous other intermediates and time consuming steps to produce the above diazo intermediate, each of which increases the process time and decreases the overall yield. Accordingly, there is a need for a fast, simple, high yield, stereoselective process for producing diazo intermediates which can be readily converted to 1-β-alkyl carbapenems.

It follows, therefore, that precursors are needed which facilitate fast and stereoselective preparation of the above-described diazo intermediates.

One such precursor is a 4-chloroazetidinone of the formula

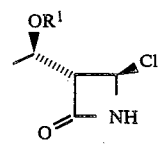

wherein $R^1$ is hydrogen or a conventional hydroxy-protecting group. However, such 4-chloroazetidinones which are unsubstituted on the 1-position nitrogen have heretofore been regarded as too unstable to produce or impossible to isolate. Accordingly, there is a need for fast, simple, high yield processes for producing 4-chloroazetidinone precursors which are unsubstituted on the 1-position nitrogen.

SUMMARY OF THE INVENTION

This invention is directed to a novel process for preparing diazo intermediates useful in the synthesis of 1-β-alkyl carbapenems, which intermediates have the formula

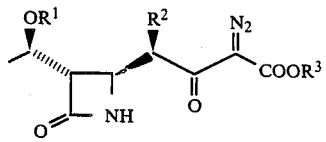

wherein $R^1$ is hydrogen or a conventional hydroxy-protecting group, $R^2$ is a lower alkyl having from 1-6 carbon atoms, and $R^3$ represents a conventional carboxyl-protecting group, which process comprises reacting a compound, in the presence of tin, a catalyst, and a polar solvent, said compound having the formula

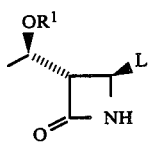

wherein $R^1$ is as defined above, and
L is a leaving group capable of being displaced by a tin enolate nucleophile of the formula

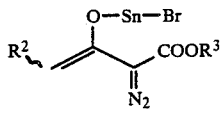

wherein $R^2$ and $R^3$ are as defined above, with a compound of the formula

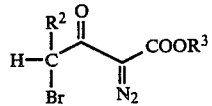

wherein $R^2$ and $R^3$ are as defined above.

The above process can be carried out quickly to yield a product having a β/α isomer ratio of approximately 3/1.

This invention also includes novel processes for preparing novel precursors of the formula

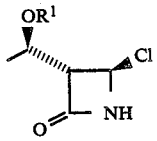

wherein $R^1$ is hydrogen or a conventional hydroxy-protecting group, which can be used to prepare diazo intermediate 14. Such precursors, which have heretofore been considered too unstable to produce and impossible to isolate, can now be quickly and easily produced in excellent yields.

DETAILED DESCRIPTION OF THE INVENTION

The process for preparing the intermediates of this invention may conveniently be summarized by the reaction sequence of Diagram 1. In this reaction, leaving group L is replaced by the tin enolate nucleophile 11 generated in the reaction mixture.

DIAGRAM 1

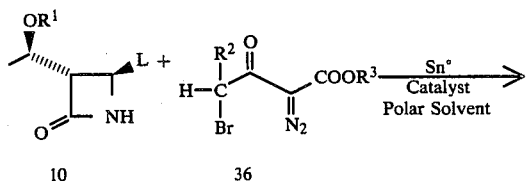

-continued
DIAGRAM 1

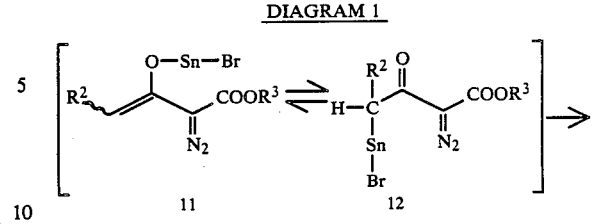

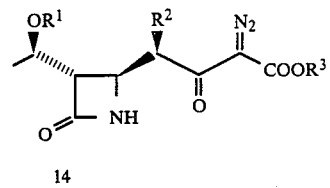

Referring now to Diagram 1, the first starting material for the synthesis is a 3,4-disubstituted azetidinone 10, wherein $R^1$ is hydrogen or a conventional hydroxy-protecting group. Hydroxy-protecting groups, which are known to those skilled in the art, are desirable because they prevent side reactions and provide increased yields in later steps of the reaction sequence. Suitable hydroxy-protecting groups may be, for example, acyl groups such as benzyloxy-carbonyl, benzhydryloxycarbonyl, trityloxycarbonyl, p-nitro-benzyloxycarbonyl and 2,2,2-trichloroethoxycarbonyl, aralkyl groups such as benzyl, benzhydryl, trityl or p-nitrobenzyl or triorganosilyl groups such as tri($C_1$-$C_6$)alkylsilyl (e.g. trimethylsilyl, triethylsilyl, triisopropylsilyl, isopropyldimethylsilyl, t-butyldimethylsilyl, methyldiisopropylsilyl or methyldi-t-butylsilyl), triarylsilyl (e.g. triphenylsilyl, tri-p-xylylsilyl) or triaralkylsilyl (e.g. tribenzylsilyl). Examples of these and other suitable hydroxy-protecting groups and methods for their formation and removal are known in the art, e.g. see *Protective Groups in Organic Synthesis*, T. W. Greene, John Wiley & Sons, New York, 1981, Chapter 2.

The hydroxy-protecting group selected is preferably one that is removable at a later stage of the reaction process. Bulky triorganosilyl groups such as triisopropylsilyl, t-butyldiphenylsilyl or t-butyldimethylsilyl are advantageously employed because they provide for an essentially stereo-controlled reduction step. Such groups can be readily removed under mild conditions, e.g. by treatment with methanolic HCl or with fluoride ion (e.g. tetra-n-butyl ammonium fluoride/tetrahydrofuran), which preserves the sensitive β-lactam nucleus.

The 4-position substituent of Compound 10 is designated by "L", which represents a leaving group capable of being displaced during the alkylation process by the tin enolate intermediate 11. Such leaving groups include acyloxy (e.g., acetoxy, propionyloxy or t-butyryloxy), halogen (e.g., chloro), arylsulfonyl (e.g., phenylsulfonyl), mesyl, tosyl, etc. Advantageously, "L" is either acetoxy or chloro because 4-acetoxyazetidinone is a readily available starting material, and, as will be discussed hereinafter, 4-chloroazetidinone possesses desirable properties as a starting material. While the discussion which follows specifically teaches this invention using these two starting materials, it is understood that the scope of the invention encompasses any azetidinone starting material having a 4-position leaving group capable of being displaced by tin enolate 11.

The other starting material for the reaction of Diagram 1 is the α-bromoketone 36, wherein $R^2$ is lower alkyl having from 1-6 carbon atoms, and $R^3$ represents a conventional carboxyl-protecting group. Carboxyl-protecting groups are well known and play an important role in carbapenem synthesis because a crucial step is the final deprotection of the C-3 ester function. Suitable carboxyl-protecting groups include $C_1$-$C_4$ alkyl, benzyl, substituted benzyl (e.g., p-nitrobenzyl), allyl, alkylallyl, arylallyl (e.g. 2-phenylallyl, 3-phenylallyl), haloallyl (e.g. 2-chloroallyl), 2-butenyl, substituted 2-butenyl (e.g. 4-methoxycarbonyl-2-butenyl), triorganosilyl groups (e.g. tri ($C_1$-$C_6$) alkylsilyl, triarylsilyl or aralkylsilyl), etc. The most advantageously employed carboxyl-protecting groups are allyl and p-nitrobenzyl, since numerous procedures have been reported for removing these groups. As will be seen in the Examples, allyl is especially advantageous because excellent yields of diazo products can be obtained which have a high $\beta/\alpha$ ratio, i.e. about 3/1. The -bromoketone 36 can be present in amounts of about 1.5-3 mole equivalents per mole equivalent of 4-acetoxyazetindinone starting material, or from about 1-5 (advantageously about 3), mole equivalents per mole equivalent of 4-chloroazetidinone starting material.

The reaction between Compound 10 and the α-bromoketone 36 is carried out in the presence of a polar solvent, tin, and a catalyst, which can be silver cations, silver cations in the form of a silver salt, such as silver nitrate or silver tetrafluoroborate, iodine, or an iodine salt such as sodium iodide or mercuric iodide.

When a 4-acetoxyazetidinone (i.e., when L is acetoxy), is employed as the starting material, a silver catalyst should be used in an amount greater than or equal to 0.1 mole equivalent per mole equivalent of the 4-acetoxyazetidinone starting material. If iodine is used as the catalyst, less than 0.1 mole equivalent per mole of the 4-acetoxyazetidinone starting material can be used, with about 0.05 mole equivalent generally being sufficient. The reaction can be carried out at a temperature of about 20°-35° C., and advantageously at about room temperature. Reaction times will vary from about 0.5-2 hours when catalyzed by silver cations, and from about 1-12 hours when catalyzed by iodine. When both silver cations and iodine are used together, the reaction will proceed almost instantaneously because iodine accelerates formation of the tin enolate. When only silver cations are used, the reaction does not proceed for about 5 minutes. The tin which is required for the reaction is advantageously supplied as activated tin in an amount of from about 1.5-3.0 mole equivalents per mole equivalent of 4-acetoxyazetidinone.

When a 4-chloroazetidinone is used as the starting material, silver catalyst should be used in an amount greater than or equal to 1 mole equivalent per mole equivalent of the 4-chloroazetidinone starting material. Iodine catalyst can be used in amounts of at least about 0.05 mole equivalents per mole equivalent of the 4-chloroazetidinone. The reaction can be run at temperatures between about 0° C. and about −70° C., advantageously at about −30° C. Reaction times will vary from about 0.25-5 hours when catalyzed by silver cations, and from about 0.25-10 hours when catalyzed by iodine. The required tin is advantageously supplied as activated tin in an amount of from about 1-8 (advantageously about 5), mole equivalents per mole equivalent of 4-chloroazetidinone.

It should be noted that when 4-chloroazetidinone is used as the starting material, a catalyst is actually not required, although yields of only a few percent will be obtained without a catalyst.

Optionally, cuprous bromide may also be added to the reaction mixture as a catalyst, although it is not required.

The reaction of Diagram 1 must be carried out in a strongly polar solvent which is advantageously DMF. Other polar solvents which can be used include DMSO, hexamethyl phosphorus amide, and dimethyl acetamide. The polar solvent can be used in pure form, but is advantageously diluted with a second solvent, which is both inert and compatible with DMF. Advantageously, the inert solvent is methylene chloride, but others such as chloroform, carbon tetrachloride, dioxane, diethyl ether, THF and dimethoxyethane can be used. The use of the inert solvent provides a cleaner reaction wherein less side products are produced. The ratio of DMF to the second solvent is advantageously not less than about 2/1 when 4-acetoxyazetidinone is the starting material because if a smaller ratio is used, the product yield of the β-isomer might be decreased. A 1/1 ratio of DMF to second solvent provides satisfactory results when 4-chloroazetidinone is the starting material.

Diagram 2 is directed to two novel processes useful in preparing 4-chloroazetidinone 27, which can be used as a starting compound in accordance with this invention.

4-Chloroazetidinone 27 can be isolated as a solid crystalline compound which is rather unstable at room temperature, but stable at −20° C. It is a white crystalline solid which is easily recrystallized from cold pentane and can be stored at −20° C. As seen above, it is a versatile intermediate for carbapenem syntheses. It has an advantage over 4-acetoxyazetidinone because reactions can be carried out at lower temperatures where 4-acetoxyazetidinone normally would not react, and 4-chloroazatidinone often yields a better stereocontrolled product.

DIAGRAM 2

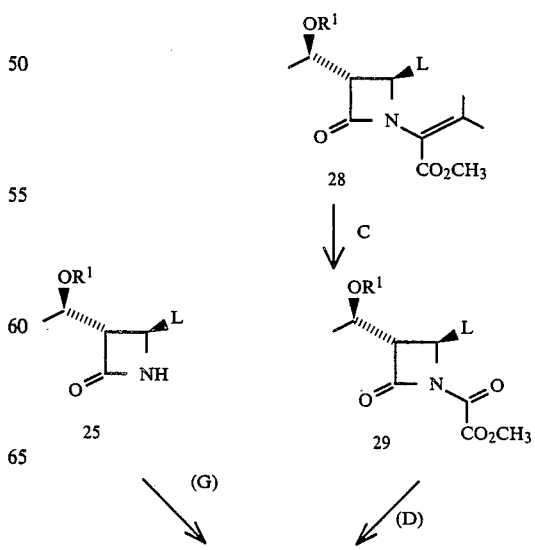

-continued
DIAGRAM 2

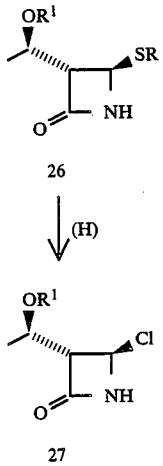

26

↓ (H)

27

Referring now to Diagram 2, Compound 27 can be prepared in good yields by chlorinolysis of the sulfide 26 using one or more mole equivalents of chlorine. Advantageously, however, an excess of chlorine is employed because when only one equivalent is used, side products can be formed which render isolation of 27 difficult or impossible. It has been found that two equivalents of chlorine will provide satisfactory results. The conversion can be carried out in a nitrogen atmosphere and under cooling (advantageously to less than abut 0° C.), by dissolving Compound 26 in a solvent such as dichloromethane, and adding an excess of chlorine for up to a few hours to yield 27. The excess chlorine can be in the form of, for example, chlorine gas which is bubbled into the solution, or it can be in the form of a solution of chlorine in carbon tetrachloride.

The precursor of 27, i.e. Compound 26, is a very stable compound which can be prepared from various starting materials, of which one is a 4-position substituted azetidinone 25, which is unsubstituted on the 1-position nitrogen.

In the conversion of Compound 25 to Compound 26, as shown in Step (G), the 4position leaving group "L" is replaced with the residue of an S-nucleophile such as an aliphatic, aromatic, araliphatic, or heterocyclic thiol compound. S-nucleophiles can also be employed in the form of a salt such as an alkali metal salt (e.g. sodium salt, potassium salt, etc.), or an alkaline-earth metal salt (e.g., magnesium salt, calcium salt, etc.), or the like. Thus, R comprises a radical selected from the group consisting of substituted and unsubstituted: alkyl, alkenyl, and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atom; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties having 1-6 carbon atoms. Advantageously, the residue is thioalkyl, thioaryl, or thioarylalkyl. Examples of suitable S-nucleophiles are t-butylmercaptan, ethylmercaptan, and their sodium salts.

It follows, therefore, that the 4-substituted azetidinones which can be used in the reaction of Step (G) are those with 4-position leaving groups which can be replaced by the residue of an S-nucleophile upon reaction with an S-nucleophile or the salt thereof. Suitable leaving groups include those previously discussed such as acyloxy, halogen (except, of course, chloro), arylsulfonyl (e.g., phenylsulfonyl), mesyl, tosyl, etc. 4-Acetoxyazetidinone is preferred because of its availability.

When an S-nucleophile is used (as opposed to an S-nucleophile salt), an organic base and a Lewis acid catalyst must be present. Suitable organic bases include organic amine bases such as triethylamine, trimethylamine, triisopropylamine, etc. Suitable Lewis acid catalysts include zinc chloride, zinc iodide, zinc bromide, titanium tetrachloride, magnesium bromide, boron trifluoride, aluminum chloride, stannic chloride trimethyltrifluoromethyl-sulfonate, and ferric chloride. Advantageously, triethylamine is the organic base, and zinc chloride is the Lewis acid catalyst. An inert solvent such as dichloromethane can also be employed. The reactants can be employed on an approximately equimolar basis, and the reaction can be run at a temperature of from about −20° C. to about 20° C., and advantageously at about 0° C. Reaction times vary from about 2 hours to about 5 days depending upon the reaction temperature.

When the salt of an S-nucleophile is used, an alcoholic solvent is required instead of an organic base and Lewis acid catalyst. Suitable alcoholic solvents include methanol, ethanol, propanol, isopropanol, butanol, etc. Advantageously, ethanol is used, and methanol is avoided because it also produces unwanted side products such as 4-methoxyazetidinone.

Step (D) of Diagram 2 illustrates an alternate route for producing Compound 26 using an N-substituted azetidinone. In Step (D), the 4-position is replaced with an S-nucleophile residue and the 1-nitrogen substituent is cleaved. The reaction can be carried out substantially as described above by reacting Compound 29 with an S-nucleophile or the salt thereof.

The most convenient starting material for the conversion of Step (D) is the chlorooxamate or acetoxyoxamate, i.e., where "L" is chloro or acetoxy. A procedure for making these compounds and their corresponding secopenams 28 has been reported by Girijavallabhan et al, Tet. Lett., 22, 3485 (1981), the contents of which are expressly incorporated herein.

Reaction times for the conversion of the chlorooxamate can be from about 0.1-5 hours at reaction temperatures of from about −20° C. to about 20° C. The reaction is advantageously carried out at about 5°-10° C., and approximately equimolar amounts of reactants can be used.

Reaction times for the conversion of the acetoxyoxamate are from about 2 hours to about 5 days at reaction temperatures of from about −20° C. to about 40° C. The reaction is advantageously carried out at about room temperature, and approximately equimolar amounts of reactants can be used.

Compound 29 can be prepared by conventional ozonolysis from its corresponding secopenam 29. The ozonolysis can be carried out by reacting 28, in a nitrogen atmosphere, with a large excess of ozone, at a temperature of less than about −20° C., and advantageously at about −78° C., which temperature can be generated easily by mixing dry ice and acetone. An excess of ozone in the solution is indicated by a persisting blue color. The excess ozone can be removed by treating the solution with nitrogen gas and by reacting the solution with dimethyl sulfide at about room temperature for about 0.5 to 4 hours.

In Diagram 2, $R^1$ represents hydrogen or a conventional hydroxy-protecting group, which groups are described above in connection with Diagram 1.

Diagram 3 illustrates a process for preparing the α-bromoketone compounds 36 which can be used as starting materials in accordance with this invention.

DIAGRAM 3

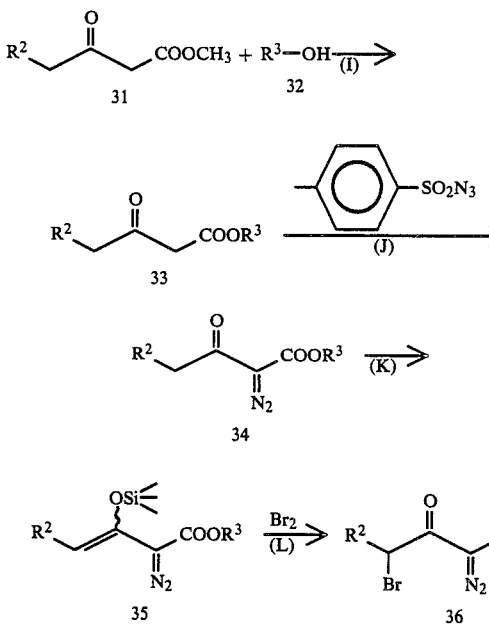

Referring now to Diagram 3, Compound 33 (wherein $R^2$ is lower alkyl having 1-6 carbon atoms, and $R^3$ is a carboxyl-protecting group as discussed above), can be prepared by an ester exchange between Compounds 31 and 32 as shown in Step (I). Formation of the 2-diazo ester 34 can be accomplished in Step (J) by reacting Compound 33 with tosyl azide in the presence of an organic base such as triethylamine.

The silyl enolate 35 of Compound 34 can be generated by reacting Compound 34 with a triorganosilyl triflate silylating agent in an inert organic solvent and in the presence of an organic base. Suitable inert organic solvents which can be used include methylene chloride, tetrahydrofuran, carbon tetrachloride, dioxane, dimethoxyethane, diethyl ether and chloroform. Reaction temperatures can be the range of from about −40° C. to +30° C. Most conveniently the reaction is carried out at a temperature of about 0°-5° C.

The triorganosilyl triflate silylating agent can be any trialkyl ($C_1$-$C_4$ alkyl) silyl trifluoromethanesulfonate such as trimethylsilyl trifluoromethanesulfonate, triisopropylsilyl trifluoromethanesulfonate, triethylsilyl trifluoromethylsulfonate, t-butyldimethylsilyl trifluoromethanesulfonate, t-butyldiphenylsilyl trifluoromethanesulfonate, or 2, 4, 6,-tri(t-butylphenoxy) dimethylsilyl trifluoromethanesulfonate. The most advantageous silylating agent is trimethylsilyl trifluoromethanesulfonate.

Suitable organic amine bases include diisopropylethylamine, DBU (1,8-diazabicyclo[5.4.0]undec-7-ene), DBN (1,5-diazabicyclo[4.3.0]non-5-ene) and especially tri($C_1$-$C_4$)alkylamines such as trimethylamine, triethylamine, tributylamine and tripropylamine.

Generally the organic base, triorganosilyl triflate and Compound 34 are reacted in approximately equimolar amounts with the base being used in slight excess. The most advantageous molar ratio of Compound 34:triorganosilyl triflate:base is about 1:1.2:1.4.

Methods for forming the silyl enolate of diazo esters are described in co-pending U.S. patent application Ser. No. 725,594 filed Apr. 22, 1985, and patented July 28, 1987 as U.S. Pat. No. 4,683,296 which application is a continuation-in-part of U.S. patent application Ser. No. 472,443 filed Mar. 7, 1983 and now abandoned. These applications are expressly incorporated herein by reference.

The silyl enolate 35 can then be reacted for about 0.1-2 hours with an equimolar amount of bromine at a temperature of about 0° C. to yield Compound 36.

Advantageously, in the reaction of Diagram 3, $R^2$ is methyl and $R^3$ is allyl. By using an allyl group in the $R^3$ position, the corresponding diazo intermediate 14 will contain an allyloxycarbonyl group, which, as previously discussed, is a well known protecting group for carboxylic acids.

The following examples illustrate the best modes contemplated for carrying out this invention.

Example 1, illustrates a transesterification as shown in Step (I) of Diagram 3, wherein $R^2$ is methyl, and $R^3$ is allyl.

EXAMPLE 1

Preparation of Allyl 3-Ketopentanoate

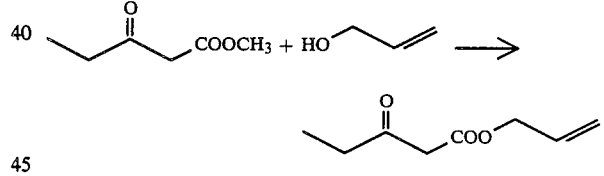

A mixture of 35 g of methyl-3-ketopentanoate and 36 mL of allyl alcohol are distilled to about 120° to 125° C., removing both methyl alcohol and allyl alcohol. Allyl alcohol (36 mL) is added to the reaction mixture, which is again distilled at 120°-125° C. This process is repeated for a total of four 36 mL portions of allyl alcohol over a 24 hour period. The remaining mixture is then vacuum distilled to yield 38.03 g of allyl-3-ketopentanoate (90% yield), bp 90°-95° C. under 10-14 mm Hg.

Example 2 illustrates Step (J) of Diagram 3, wherein a diazo group is introduced onto the 2-position carbon of allyl 3-ketopentanoate.

EXAMPLE 2

Preparation of Allyl 2-diazo-3-ketopentanoate

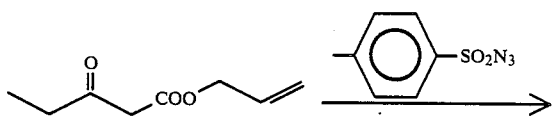

-continued

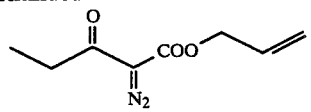

To a reaction vessel, 1,000 mL of reagent grade acetonitrile is added and agitation is begun. Sodium azide (68.26 g, 1.05 mole) is added, followed by 190.6 g of p-toluenesulfonyl chloride (1.0 mole). The reaction is stirred at room temperature (23° C.) until completion, which is indicated by the disappearance of tosyl chloride in TLC. The reaction is usually complete within about 10 hours. Poor agitation or excessive sodium azide particle size may prolong completion. At 55° C., the reaction is usually complete in about 2 hours. At this point, the sodium chloride can be filtered, or it can be carried along and filtered later with the tosyl amide precipitate (which is a by-product of the reaction between allyl 3-ketopentanoate and tosyl azide) if the reaction vessel outlet can handle the thick mixture. After the tosyl azide preparation is complete, 14 mL of triethylamine (0.10 mole) is added to the reaction mixture at 10°-15° C. A solution of allyl 3-ketopentanoate (156.2 g, 1.0 mole) in 142 mL of acetonitrile is added dropwise at a rate that will maintain the temperature at about 10°-20° C. An exotherm should be observed during the addition, otherwise no reaction is occurring. If no reaction is occurring, the mixture should be checked to insure that it is sufficiently basic.

The reaction mixture is stirred for 30 minutes or more at/or under 20° C., and the temperature is then raised to 20°-25° C. The mixture is stirred an additional hour at 20°-25° C. and analyzed by TLC for completion. Once the reaction is complete, the mixture can be concentrated in vacuo to 2.1-2.6 L per kg of input acetoacetate while maintaining the mixture at 40° C. or less. The thick mixture is then diluted with 750 mL of heptane followed by reconcentration in vacuo to 4.5-5.0 L per kg propionylacetate input. The concentrated mixture is again diluted with heptane (500 mL) and stirred for about 15 minutes. The slurry is filtered and the solids are washed with 250 mL heptane, combining the wash with the filtrate. The combined heptane solution is then washed with 500 mL of 1N HCl and the lower aqueous phase is discarded. The heptane solution is dried with sufficient sodium sulfate or magnesium sulfate, and then concentrated in vacuo, while maintaining an internal temperature of less than 40° C. The title compound is obtained as a yellow oil in a 92% yield.

Example 3 illustrates the formation of the silyl enolate of allyl 2-diazo-3-ketopentanoate, followed by bromination to yield allyl 2-diazo-3-keto-4-bromopentanoate, as shown in Steps (K) and (L) of Diagram 3.

EXAMPLE 3

Preparation of Allyl 2-diazo-3-keto-4-bromopentanoate

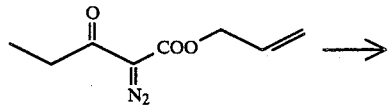

-continued

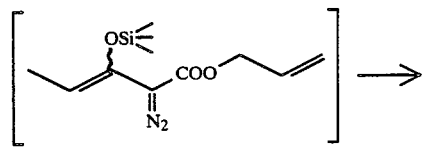

To an ice-cooled solution of allyl 2-diazo-3-ketopentanoate (9.1 g, 0.05 mole) in 100 mL of $CH_2CL_2$, was added 8.35 mL of triethylamine, followed by dropwise addition of 11.6 mL trimethylsilyl triflate (13.34 g, 0.06 mole) over twenty minutes. The resulting solution (orange) was stirred at 0° C. for one hour. A solution of bromine (8.0 g, 0.05 mole) in 30 mL $CH_2Cl_2$ was added over twenty minutes at 0° C. The mixture was stirred at 0° C. for one hour. The reaction mixture was then washed with water three times, dried over magnesium sulphate and concentrated to give the title compound as an oil (12.74 G, 97% yield).

Examples 4-8 relate to Diagram 2, wherein $R^1$ is t-butyldimethylsilyl.

Example 4 describes the procedure used to prepare starting material 22 (i.e., Compound 28 wherein L is chloro).

EXAMPLE 4

Preparation of (3S,4R)-3-[1(R)-t-Butyldimethylsilyloxyethyl]-4-chloro-1-(1-methoxycarbonyl-2-methyl-1-propenyl)azetidin-2-one (22)

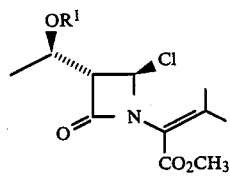

Compound 22 was prepared in the same manner as described by Girijavallabhan et al, *Tet. Lett.*, 22, 3485 (1981), using a t-butyldimethylsilyl group to protect the hydroxy group instead of trichloroethyl carbonate. The crude solid was used without further purification.

NMR (60 MHz, CDCl$_3$) δ: 0.03 (s, 6H, CH$_3$—Si), 0.83 (s, 9H, CH$_3$—C—Si), 1.23 (d, J=6 Hz, 3H, CH$_3$—CH—O), 1.93, 2.22 (2s, 6H, =C(CH$_3$)$_2$), 3.32 (dd, J=1.5 Hz, 1H, H-3), 3.71 (s, 3H, CO$_2$CH$_3$), 4.18 (m, 1H, CH$_3$—CH—O), 5.86 (d, J=1.5 Hz, 1H, H-4).

Example 5 describes a procedure for preparing Compound 24 (i.e., Compound 29, wherein L is chloro).

EXAMPLE 5

Preparation of (3S,4R)-3-[1(R)-t-Butyldimethylsilyloxyethyl]-4-chloro-1-(2-methoxy-1,2-dioxyethyl)azetidin-2-one (24)

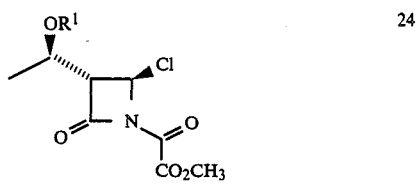

24

Compound 24 was prepared in same manner as described by Girijavallabhan et al, *Tet. Lett.*, 22, 3485 (1981), using t-butyldimethylsilyl group as protection of the hydroxy group instead of trichloroethyl carbonate. The crude solid was used without purification, and was unstable on silica gel TLC plate.

NMR (200 MHz, CDCl$_3$) δ: 0.01, 0.06 (2s, 6H, CH$_3$—Si), 0.81 (s, 9H, CH$_3$—C—Si), 1.28 (d, J=6.3 Hz, 3H, CH$_3$—CH—O), 3.53 (overlapping dd, 1H, H-3), 3.92 (s, 3H, CO$_2$CH$_3$), 4.32 (m, 1H, CH$_3$—CH—O), 6.01 (d, J=1.9 Hz, 1H, H-4). IR (nujol): 1715, 1760, 1825 cm$^{-1}$.

Example 6 illustrates the conversion shown in Step (C) of Diagram 2, wherein L is acetoxy.

EXAMPLE 6

Preparation of (3S,4R)-4-Acetoxy-3-[1(R)-t-butyldimethylsilyloxyethyl]-1-(2-methoxy-1,2-dioxyethyl)azetidin-2-one (23)

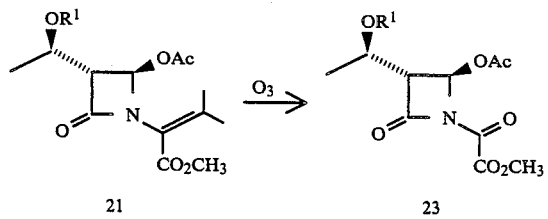

A solution of 21 (7.98 g) in CH$_2$Cl$_2$ (80 mL) was cooled to −78° C. and ozone gas was bubbled into the solution until blue color persisted. The cooling bath was removed and the excess ozone was expelled by bubbling nitrogen gas into the solution. The ozonide solution was treated at room temperature with dimethyl sulfide (3 mL) for 1.5 hours. The clear colorless solution was washed three times with water, dried over anhydrous MgSO$_4$ and concentrated to give the white crystalline title compound. Yield 7.7 g (98%), mp 47° C.

NMR (200 MHz, CDCl$_3$) δ: 0.01, 0.06 (2s, 6H, CH$_3$—Si), 0.81 (s, 9H, CH$_3$—C—Si), 1.29 (d, J=6.4 Hz, 3H, CH$_3$—CH—O), 2.11 (s, 3H, OCOCH$_3$), 3.26 (dd, J=1.9 and 2.0 Hz, 1H, H-3), 3.90 (s, 3H, CO$_2$CH$_3$), 4.31 (m, 1H, CH$_3$—CH—O), 6.73 (d, J=2.0 Hz, 1H, H-4). IR (nujol): 1700, 1760, 1828 cm$^{-1}$.

Example 7 illustrates three methods for forming Compound 26, using as the starting materials, 4-acetoxyazetidinone 20, chlorooaxamate 24, and acetoxyoxamate 23.

EXAMPLE 7

Preparation of (3S,4R)-3-[1(R)-t-Butyldimethylsilyloxyethyl]-4-t-butylthioazetidin-2-one (26)

Method A: via 4-acetoxyazetidinone 20

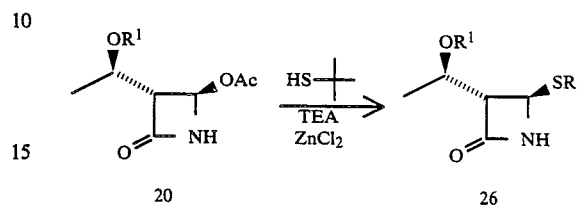

To a solution of 25 (57.4 g, 0.2 mole) in CH$_2$Cl$_2$ (600 mL) was added t-butylmercaptane (24.6 mL, 0.22 mole), followed by addition of triethylamine (30.6 mL, 0.22 mole). The solution was cooled to 0° C. and zinc chloride (27.2 g, 0.2 mole) was added. The resulting milky solution was stirred at room temperature for two days. The reaction mixture was successively washed with 1N HCl (500 mL), saturated NaHCO$_3$ (500 mL), and water (500 mL), dried over anhydrous MgSO$_4$ and concentrated to give a wet crystalline solid (70 g) which was triturated in isopropyl alcohol (150 mL) and then diluted with water (150 mL). The slurry was cooled to 5° C. and filtered. The cake was washed with cold (5° C.) isopropyl alcohol/water (1:2, 100 mL) and dried in vacuo. The yield was 44.3 g (70%); mp 152°–154° C.;

NMR (200 MHz, CDCl$_3$); δ0.06, 0.07 (2s, 6H, CH$_3$—Si), 0.87 (s, 9H, CH$_3$—C—Si), 1.20 (d, J=6.3 Hz, 3H, CH$_3$—CH—O), 1.36 (s, 9H, S—CH$_3$), 3.03 (m, 1H, H-3), 4.25 (m, 1H, CH$_3$—CH—O), 5.00 (d, J=2.6 Hz, 1H, H-4), 6.06 (broad s, 1H, NH). IR (nujol): 1715, 1762 cm$^{-1}$.

Method B: via chlorooxamate 24

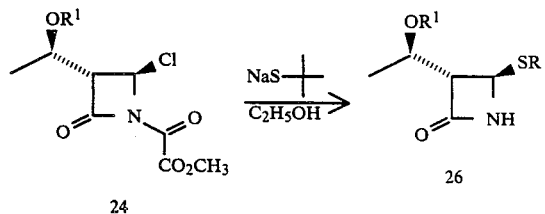

To an ice-cooled solution of 24 (0.349 g, 1 mmol) in ethanol (5 mL) was dropwise added sodium t-butylmercaptide (1.1 mL of 1M solution in EtOH/H$_2$O 6:1). The resulting solution was stirred at 5°–10° C. for 15 minutes. The reaction mixture was diluted with ether (70 mL), washed four times with brine, dried over anhydrous MgSO$_4$ and concentrated to dryness, affording the expected white crystalline product. The yield was 0.3 g (94%).

Method C: via acetoxyoxamate 23

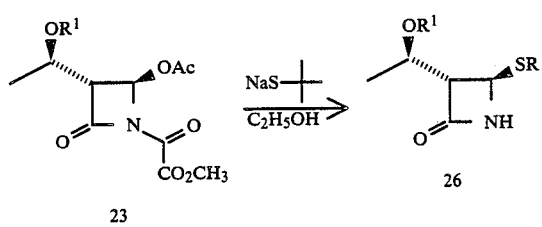

To a solution of 23 (0.389 g, 1 mmol) in ethanol (6 mL) at room temperature was dropwise added sodium t-butylmercaptide (1.1 mL, 1M solution in EtOH/H$_2$O 6:1) over 3 minutes. The reaction was exothermic and the temperature rose to 27° C. from 23° C. The resulting hazy solution was stirred at room temperature for 18 hours. The reaction mixture was diluted with ether (50 mL), washed four times with brine, dried over anhydrous MgSO$_4$ and concentrated to give the white crystalline title compound. The yield was 0.31 g (98%).

Example 8 illustrates the conversion of Compound 26 to Compound 27, as shown in Step (H) of Diagram 2.

EXAMPLE 8

Preparation of (3S,4R)-3-[1(R)-t-Butyldimethylsilyloxyethyl]-4-chloroazetidin-2-one (27)

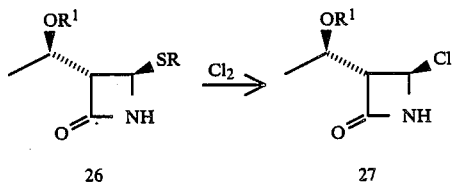

Compound 26 (5.0 g, 15.77 mmol) was dissolved in CH$_2$Cl$_2$ (50 mL) and cooled to −15° C. Then, chlorine gas (2.24 g, 31.54 mmol) was gently bubbled in, maintaining the temperature between −5° C. and −15° C. The reaction mixture was concentrated to give a crystalline solid which was recrystallized from cold (−70° C.) pentane. The yield was 3.12 g (76%), white crystals, mp 85° C.

NMR (200 MHz, CDCl$_3$) δ0.03, 0.05 (2s, 6H, $\underline{CH_3}$—Si), 0.84 (s, 9H, $\underline{CH_3}$—C—Si), 1.26 (d, J=6.4 Hz, 3H, $\underline{CH_3}$—CH—O), 3.41 (m, 1H, H-3), 4.21 (m, 1H, CH$_3$—$\underline{CH}$—O), 5.67 (d, J=1.3 Hz, 1H, H-4), 6.25 (broad s, 1H, NH). IR (Nujol): 1736, 1775 cm$^{-1}$.

Examples 9 and 10 illustrate the conversion shown in Diagram 1 using iodine as the catalyst, and (3S,4R)-3-[1(R)-t-butyldimethylsilyloxyethyl]-4-acetoxyazetidin-2-one and allyl 2-diazo-3-keto-4-bromopentonoate as the starting materials.

EXAMPLE 9

Preparation of (3S,4R)-3-[1(R)-t-Butyldimethylsilyloxyethyl]-4-[1(R)-methyl-4-allyloxy-2,4-dioxybutyl]azetidin-2-one

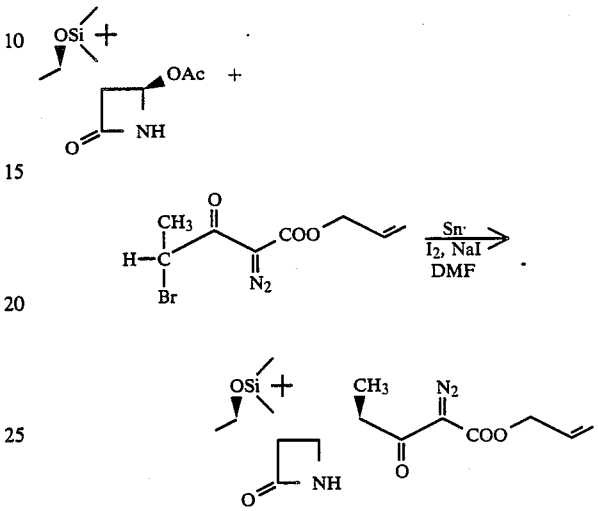

A solution of the α-bromoketone (1.098 g, 4.205 mmol) was added to a prepared mixture of the 4-acetoxyazetidinone (1.15 g, 4.00 mmol), sodium iodide (150 mg, 1.00 mmol) and activated tin (549 mg, 4.265 mmol) in 5 mL of DMF. The resulting slurry was stirred at room temperature for thirty minutes. TLC indicated that no reaction occurred. A small crystal of I$_2$ was added and a small exothermic reaction indicated that the reaction had begun. The mixture was stirred at room temperature for five hours and then cooled to 0° C. before addition of 10 mL of 1N HCl. The mixture was extracted twice with 15 mL of diethyl ether and then dried. After concentration in vacuo, the title compound was contained as a light yellow oil (1.417 g). HPLC indicated a β/α ratio of 74.6/28.5, and thus the overall β-yield was 18%.

EXAMPLE 10

Preparation of (3S,4R)-3-[1(R)-t-Butyldimethylsilyloxyethyl]-4-[1(R)-methyl-4-allyloxy-2,4-dioxybutyl]azetidin-2-one

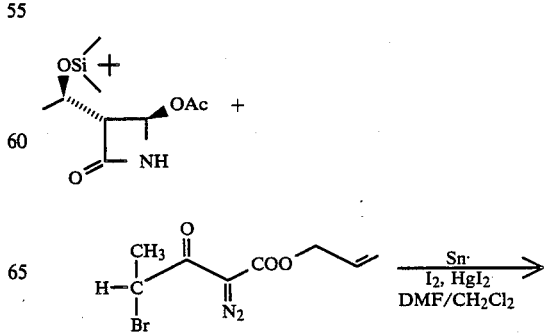

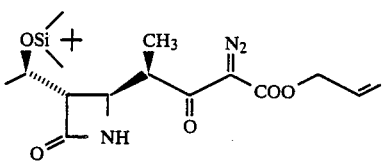

Mercuric iodide (248 mg, 0.548 mmol) was added to a stirred suspension of activated tin (2.60 g, 21.91 mmol) in 5 mL of a 2:1 mixture of DMF/CH$_2$Cl$_2$. The slurry was stirred at room temperature for fifteen minutes, and the 4-acetoxyazetidinone (786 mg, 2.74 mmol) was added. The α-bromoketone (1.43 g, 5.479 mmol) was dissolved in 10 mL of a 2:1 DMF/CH$_2$Cl$_2$ mixture and half of the volume was quickly added followed by addition of a small crystal of iodine (approximately 40 mg). The mixture was stirred at room temperature for 2.5 hours, followed by addition of the remaining α-bromoketone solution. The mixture was stirred overnight. The solids were separated by filtration over a fiberglass paper and washed with 15 mL of ethyl acetate. The filtrate (cloudy) was poured into 50 mL of ethyl acetate and washed with 15 mL of 1N HCl. The aqueous phase was collected and extracted with 15 mL of ethyl acetate. The combined organic layers were washed once with 25 mL of 1N HCl, and twice with 25 mL of brine. After drying over magnesium sulfate, the solution was filtered through a pad of silica gel (10 mL) and after evaporation of the filtrate, 2.451 grams of the title compound was obtained as a yellow slurry. HPLC indicated the yield to be 41.32%, of which the β/α ratio was 77/23.

Examples 11 and 12 utilize the same starting materials as Examples 9 and 10, but additionally use silver cations to catalyze the reaction.

EXAMPLE 11

Preparation of
(3S,4R)-3-[1(R)-t-Butyldimethylsilyloxyethyl]-4-[1(R)-methyl-4-allyloxy-2,4-dioxybutyl]azetidin-2-one

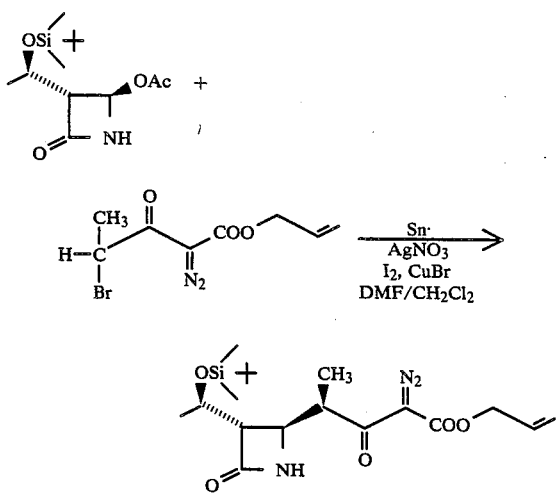

Silver nitrate (661 mg, 3.89 mmol) was added to a vigorously stirred mixture of activated tin (10.16 g, 85.60 mmol), CuBr (70 mg), 4-acetoxyazetidinone (11.17 g, 38.91 mmol) and α-bromoketone (20.31 g, 77.82 mmol) in a 2:1 DMF/CH$_2$Cl$_2$ mixture. The resulting black suspension was stirred for five minutes and then a crystal of iodine (300 mg) was added. The temperature rose quickly to 30° C. and the mixture ws stirred at 30°-32° C., while controlling the temperature with a water bath of about 28° C. The mixture was stirred for 1.5 hours, at which time TLC indicated the reaction was complete. Forty mL of Florisil (which is the trademark for a highly selective absorbent of extremely white, hard granular or powered magnesia-silica gel produced by Floridin Co., 3 Penn Center, Pittsburgh, PA 15235), were added and the slurry was stirred for five minutes and then filtered through fiberglass paper into a receiver flask which contained 150 mL of 1N HCl which had been cooled to 0° C. The flask was washed with 100 mL of ethyl acetate. The filtrate was poured into 400 mL of ethyl acetate (total volume of ethyl acetate=500 mL). After shaking, the aqueous phase was discarded and the remaining solution was washed twice with 150 mL of 1N HCl and twice with 300 mL of brine. After drying and concentrating in vacuo, 24.43 g of a light yellow-orange oil was obtained. The product yield by HPLC was 45.7%, with a β/α ratio of 71/29. The crude product was treated with 150 mL of methanol and 37 mL of 2N HCl for 24 hours. The mixture was diluted with 413 mL of water and extracted three times with 200 mL of hexane, and three times with 250 mL of ethyl acetate after saturation with NaCl. The combined organic layers were washed twice with 2.5% NaOH (150 mL), 1N HCl (150 mL), water (200 mL) and brine (200 mL). After drying and concentrating in vacuo, 7.35 g of a yellow oil was obtained. The β-product yield by HPLC was 31.18%.

EXAMPLE 12

Preparation of
(3S,4R)-3-[1(R)-t-Butyldimethylsilyloxyethyl]-4-[1(R)-methyl-4-allyloxy-2,4-dioxybutyl]azetidin-2-one

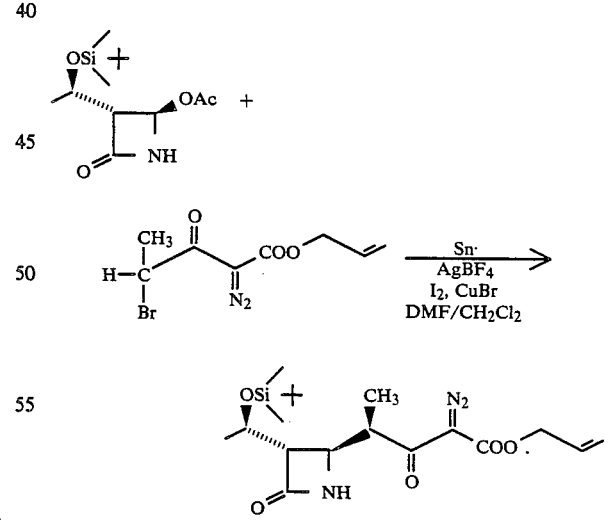

To a mixture of activated tin (10.16 g, 85.60 mmol), α-bromoketone (20.31 g, 77.82 mmol), 4-acetoxyazetidinone (11.17 g, 38.91 mmol), CuBr (60 mg) in a 2:1 mixture of DMF/CH$_2$Cl$_2$ (76 mL/38 mL), was added AgBF$_4$ (0.757 mg, 3.891 mmol). The mixture turned black and the temperature raised to 30° C. Iodine (100 mg) was added and the temperature was kept at 30°-31° C. using a water bath of about 27° C. After 45 minutes, TLC indicated the reaction was complete, and the mixture was cooled to about 5°–10° C., and 10 g of NH4Cl were added. After stirring for five minutes, 40 mL of SiO2 (230–400 mesh) were added. After stirring for five minutes, the mixture was filtered over fiberglass paper, and 150 mL of 1N HCl was added. The solids were washed with 100 mL of ethyl acetate. The filtrate was then poured into 400 mL of ethyl acetate and shaken vigorously. The aqueous layer was discarded and the organic phase was washed once with 150 mL of 1N HCl and twice with 250 mL of brine. After drying and concentrating in vacuo, the resulting slurry was treated with 60 mL of a 3/7 mixture of ethyl acetate/hexane. The solids were filtered off and washed with 40 mL of the solvent mixture. After concentration in vacuo, 26.58 g of a light orange oil were isolated. The product yield, obtained by HPLC, was 57.8%, with a β/α ratio of 73.3/26.7.

It can be seen from Examples 11–14 that silver cations are a more advantageous catalyst than iodine because they provide much faster reaction times, and an overall better yield of the β-isomer. It is also seen that AgBF4 is more efficient than AgNO3.

Example 13 illustrates the reaction between allyl 2-diazo-3-keto-4-bromopentonoate and 4-chloroazetidinone.

EXAMPLE 13

Preparation of (3S,4R)-3-[1(R)-t-Butyldimethylsilyloxyethyl]-4-[1(R)-methyl-4-allyloxy-2,4-dioxybutyl]azetidin-2-one

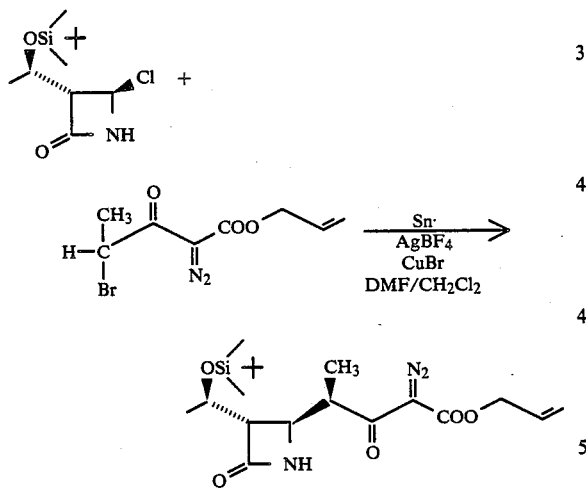

To a slurry of tin dust (1.19 g, 10 mmol) and CuBr (10 mg) in dry DMF (10 mL) at room temperature (23° C.) under nitrogen, was dropwise added a solution of α-bromoketone (1.57 g, 6 mmol) in dry CH2Cl2 (10 mL) over a 10 minute period. The reaction was slightly exothermic, exhibiting a temperature rise to approximately 26° C. The slurry was stirred for twenty minutes at room temperature, and then cooled to −70° C. 4-Chloroazetidinone (0.527 g, 2 mmol) in CH2Cl2 (3 mL) was added, followed by addition of AgBF4 (0.39 g, 2 mmol). The resulting slurry was allowed to warm to −30° C. and stirred for 35 minutes. TLC indicated the reaction was complete. The reaction mixture was then filtered on Celite (which is the trademark for diatomaceous earth and related products produced by Johns-Manville Products Corporation, Celite Division, Manville, NJ), into saturated ammonium chloride (30 mL) and the Celite pad was washed with ether. The filtrate was diluted with ether, such that the total volume of ether used was 100 mL. The filtrate was shaken and the organic layer was separated, washed with brine, dried over MgSO4 and concentrated to yield an oil (1.9 g). Silica gel chromatography yielded the desired product as a crystalline solid (0.66 g, 80.6%). The product yield of β/α by HPLC, was 74.26. The β-purity was 67.2%, and thus the overall β-yield was 53.8%.

Example 13 demonstrates that excellent yields of the β-isomer can be obtained in short reaction times using the 4-chloroazetidinone as a starting material.

What is claimed is:

1. A process for producing diazo intermediates of the formula

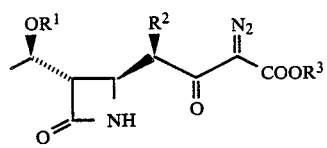

14 wherein
$R^1$ is hydrogen or a conventional hydroxy-protecting group;
$R^2$ is a lower alkyl having from 1–6 carbon atoms, and
$R^3$ represents a conventional carboxyl-protecting group, which process comprises
reacting a compound, in the presence of tin, a silver salt, iodine, or an iodide salt as catalysit and a polar solvent, said compound having the formula

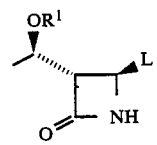

10 wherein $R^1$ is as defined above, and
L is a leaving group capable of being displaced by a tin enolate of the formula

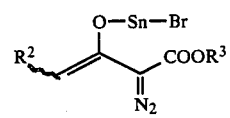

11 wherein $R^2$ and $R^3$ are as defined above, with a compound of the formula

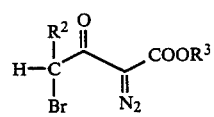

36 wherein $R^2$ and $R^3$ are as defined above.

2. The process of claim 1, wherein $R^2$ is selected from the group consisting of methyl, ethyl, propyl, and butyl.

3. The process of claim 2, wherein $R^2$ is methyl.

4. The process of claim 1, wherein

R³ is selected from the group consisting of C₁-C₄ alkyl, benzyl, substituted benzyl, allyl, alkylallyl, arylallyl, haloallyl, 2-butenyl, 4-methoxycarbonyl-2-butenyl, and triorganosilyl.

5. The process of claim 4, wherein R³ is allyl.

6. The process of claim 4, wherein R³ is p-nitrobenzyl.

7. The process of claim 3, wherein R³ is allyl.

8. The process of claim 3, wherein R³ is p-nitrobenzyl.

9. A process for producing diazo intermediates of the formula

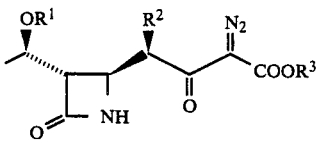

wherein R¹ is hydrogen or a conventional hydroxy-protecting group,
R² is a lower alkyl having from 1–6 carbon atoms, and
R³ represents a conventional carboxyl-protecting group, which process comprises
reacting a compound, in the presence of tin, a silver salt, iodine, or an iodide salt as catalyst, and a polar solvent, said compound having the formula

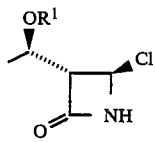

wherein R¹ is as defined above, with a compound of the formula

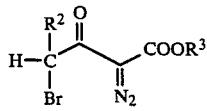

wherein R² and R³ are as defined above.

10. The process of claim 1, wherein said silver salt is silver nitrate or silver tetrafluoroborate.

11. The process of claim 1, wherein said leaving group is acetoxy or chlorine.

12. The process of claim 11, wherein R² is methyl,
R³ is allyl, and
said catalyst is selected from the group consisting of silver cations, silver salt, iodine, and iodine salt.

13. The process of claim 12, wherein said polar solvent is DMF.

14. A process for producing diazo intermediates of the formula

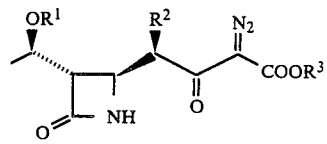

wherein R¹ is hydrogen or a conventional hydroxy-protecting group,
R² is a lower alkyl having from 1–6 carbon atoms, and
R³ represents a conventional carboxyl-protecting group,
which process comprises
reacting a compound, in the presence of tin, a silver salt, iodine, or an iodide salt as catalyst, and a polar solvent, said compound having the formula

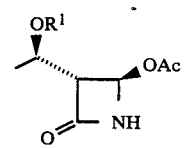

wherein R¹ is a defined above and Ac is acetyl, with a compound of the formula

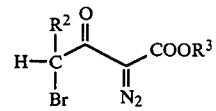

wherein R² and R³ are as defined above.

15. The process of claim 14, wherein R² is selected from the group consisting of methyl, ethyl, propyl, and butyl.

16. The process of claim 15, wherein R² is methyl.

17. The process of claim 14, wherein R³ is selected from the group consisting of C₁-C₄ alkyl, benzyl, substituted benzyl, allyl, alkylallyl, arylallyl, haloallyl, 2-butenyl, substituted 2-butenyl, and triorganosilyl.

18. The process of claim 17, wherein R³ is allyl.

19. The process of claim 17, wherein R³ is p-nitrobenzyl.

20. The process of claim 16, wherein R³ is allyl.

21. The process of claim 16, wherein R³ is p-nitrobenzyl.

22. The process of claim 9, wherein said silver salt is silver nitrate or silver tetrafluoroborate.

23. The process of claim 14, wherein said silver salt is silver nitrate or silver tetrafluoroborate.

24. The process of claim 20, wherein said catalyst is selected from the group consisting of silver cations, silver salt, iodine and iodine salt.

25. The process of claim 24, wherein said polar solvent is DMF.

26. The process of claim 9, wherein R² is selected from the group consisting of methyl, ethyl, propyl, and butyl.

27. The process of claim 26, wherein R² is methyl.

28. The process of claim 27, wherein R$^3$ is p-nitrobenyl.

29. The process of claim 9, wherein R$^3$ is selected from the group consisting of C$_1$–C$_4$ alkyl, benzyl, substituted benzyl, allyl, alkylallyl, arylallyl, haloallyl, 2-butenyl, substituted 2-butenyl, and triorganosilyl.

30. The process of claim 29, wherein R$^3$ is allyl.

31. The process of claim 29, wherein R$^3$ is p-nitrobenzyl.

32. The process of claim 27, wherein R$^3$ is allyl.

33. The process of claim 32, wherein said catalyst is selected from the group consisting of silver cations, silver salt, iodine and iodine salt.

34. The process of claim 33, wherein said polar solvent is DMF.

* * * * *